United States Patent
Marcella

(10) Patent No.: US 10,136,682 B1
(45) Date of Patent: Nov. 27, 2018

(54) BREAST-LIFTING AND COOLING ACCESSORY

(71) Applicant: Jacqueline Butler Marcella, Washington, PA (US)

(72) Inventor: Jacqueline Butler Marcella, Washington, PA (US)

( * ) Notice: Subject to any disclaimer, the term of this patent is extended or adjusted under 35 U.S.C. 154(b) by 0 days.

(21) Appl. No.: 15/701,600

(22) Filed: Sep. 12, 2017

(51) Int. Cl.
  *A41C 3/00* (2006.01)
  *A41C 3/06* (2006.01)
  *A61F 7/02* (2006.01)

(52) U.S. Cl.
  CPC ............ *A41C 3/0064* (2013.01); *A41C 3/065* (2013.01); *A61F 7/02* (2013.01); *A61F 2007/0226* (2013.01); *A61F 2007/0234* (2013.01)

(58) Field of Classification Search
  CPC .......................................................... A61F 7/02
  USPC .................. 450/81, 37, 54–57; 2/53, 55, 46
  See application file for complete search history.

(56) References Cited

U.S. PATENT DOCUMENTS

| | | | |
|---|---|---|---|
| 5,098,330 A | 3/1992 | Greenberg | |
| 5,441,534 A * | 8/1995 | MacWinnie | A61F 7/02 383/901 |
| 5,507,794 A * | 4/1996 | Allen | A61F 7/02 126/204 |
| 5,679,052 A * | 10/1997 | Rucki | A61F 7/02 2/267 |
| 5,776,177 A * | 7/1998 | MacWhinnie | A61F 7/02 128/890 |
| 5,980,359 A * | 11/1999 | Brown | A41C 3/12 450/14 |
| 6,203,399 B1 * | 3/2001 | Hackney | A41C 3/00 2/267 |
| 6,237,599 B1 | 5/2001 | Maulding | |
| 6,241,718 B1 * | 6/2001 | Arless | A61B 18/02 604/509 |
| 6,383,055 B2 | 5/2002 | Valentin | |
| 7,077,719 B2 | 7/2006 | Shiekman | |
| 7,429,206 B2 | 9/2008 | Perry | |
| 7,585,200 B1 * | 9/2009 | McLaren | A41C 3/0035 2/247 |
| 7,905,763 B1 * | 3/2011 | Frank | A61F 13/141 450/37 |
| 8,075,367 B2 * | 12/2011 | Taylor | A41C 3/10 2/53 |
| D662,279 S | 6/2012 | Chang | |
| 8,506,350 B1 | 8/2013 | Silverman | |
| 8,911,416 B2 * | 12/2014 | Johnson | A41D 27/12 450/37 |

(Continued)

*Primary Examiner* — Gloria Hale
(74) *Attorney, Agent, or Firm* — Kyle A. Fletcher, Esq.

(57) ABSTRACT

The breast-lifting and cooling accessory is a therapeutic garment. The breast-lifting and cooling accessory is configured for use with a woman. The woman is further defined with a left breast, a right breast, an intermammary cleft, and a sternum. The breast-lifting and cooling accessory is a supporting garment that elevates the breasts with or without a brassiere. The breast-lifting and cooling accessory is a self-attaching garment. The breast-lifting and cooling accessory is a thermal structure that can further be used to cool the left breast and the right breast of the woman. The breast-lifting and cooling accessory comprises a left support, a right support, and a sternum structure. The left support and the right support are joined at the sternum structure.

18 Claims, 3 Drawing Sheets

(56) References Cited

U.S. PATENT DOCUMENTS

| | | | | |
|---|---|---|---|---|
| 2003/0023216 A1* | 1/2003 | Carlucci | A61L 15/22 | 604/375 |
| 2003/0023291 A1* | 1/2003 | Hanner | A61F 7/02 | 607/108 |
| 2005/0175665 A1* | 8/2005 | Hunter | A61K 45/06 | 424/423 |
| 2005/0260921 A1* | 11/2005 | Silver | A41C 3/065 | 450/81 |
| 2007/0225783 A1* | 9/2007 | Koby | A61F 7/02 | 607/108 |
| 2008/0195185 A1* | 8/2008 | Krempel | A61F 7/02 | 607/108 |
| 2008/0312616 A1 | 12/2008 | Nixon | | |
| 2009/0117825 A1 | 5/2009 | Lutzi | | |
| 2009/0248121 A1* | 10/2009 | Miller | A61F 7/02 | 607/108 |
| 2010/0029176 A1* | 2/2010 | Chen | A41C 3/065 | 450/38 |
| 2010/0048098 A1* | 2/2010 | Rosario | A41C 3/0035 | 450/57 |
| 2010/0101586 A1* | 4/2010 | Frye | A41C 3/14 | 128/889 |
| 2010/0105286 A1* | 4/2010 | Frye | A61F 13/145 | 450/57 |
| 2011/0106227 A1* | 5/2011 | Desiderio | A61F 7/02 | 607/111 |
| 2011/0256801 A1* | 10/2011 | Cho | A41C 3/065 | 450/39 |
| 2012/0071955 A1* | 3/2012 | Yockel | A61F 7/02 | 607/114 |
| 2012/0083863 A1* | 4/2012 | Gillespie | A41C 3/146 | 607/108 |
| 2014/0045408 A1* | 2/2014 | Yung | A41C 3/122 | 450/41 |
| 2014/0302745 A1 | 10/2014 | Golubovic | | |
| 2014/0370784 A1* | 12/2014 | Chen | A41O 5/005 | 450/41 |
| 2015/0209468 A1* | 7/2015 | Aviles | A61F 13/84 | 424/402 |
| 2016/0095743 A1* | 4/2016 | Jackson | A61F 7/02 | 607/108 |
| 2016/0354507 A1* | 12/2016 | Aviles | A61L 15/40 | |

\* cited by examiner

BREAST-LIFTING AND COOLING ACCESSORY

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of personal or domestic articles including wearing apparel, more specifically, a strapless brassiere attached directly to the body by means of an adhesive, if necessary.

SUMMARY OF INVENTION

The breast-lifting and cooling accessory is a therapeutic garment. The breast-lifting and cooling accessory is configured for use with a woman. The woman is further defined with a left breast, a right breast, an intermammary cleft, and a sternum. The breast-lifting and cooling accessory is a supporting garment that elevates and cools the breasts with our without a brassiere. The breast-lifting and cooling accessory is a self-attaching garment. The breast-lifting and cooling accessory is a thermal structure that can be used to cool the left breast and the right breast of the woman. The breast-lifting and cooling accessory comprises a left support, a right support, and a sternum structure. The left support and the right support are joined at the sternum structure.

These together with additional objects, features and advantages of the breast-lifting and cooling accessory will be readily apparent to those of ordinary skill in the art upon reading the following detailed description of the presently preferred, but nonetheless illustrative, embodiments when taken in conjunction with the accompanying drawings.

In this respect, before explaining the current embodiments of the breast-lifting and cooling accessory in detail, it is to be understood that the breast-lifting and cooling accessory is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the breast-lifting and cooling accessory.

It is therefore important that the claims be regarded as including such equivalent construction insofar as they do not depart from the spirit and scope of the breast-lifting and cooling accessory. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
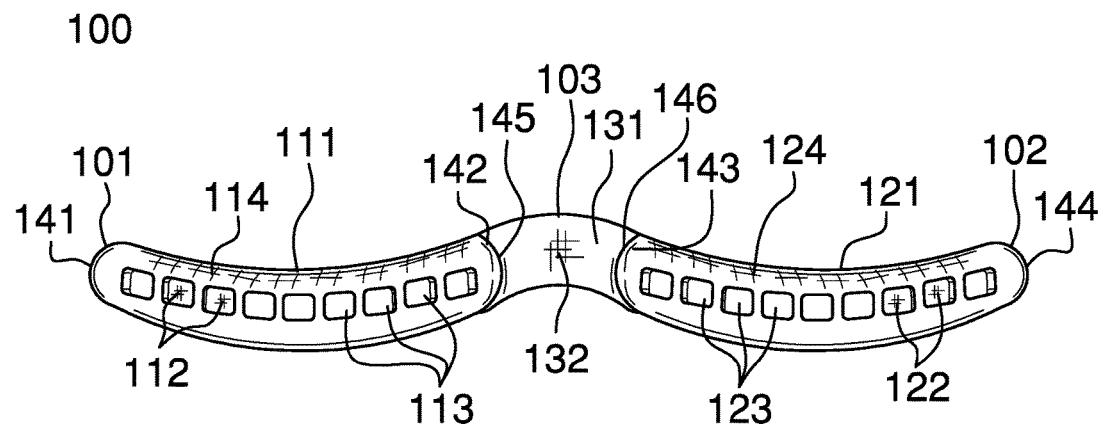
FIG. 1 is a front view of an embodiment of the disclosure.
Figure 2:
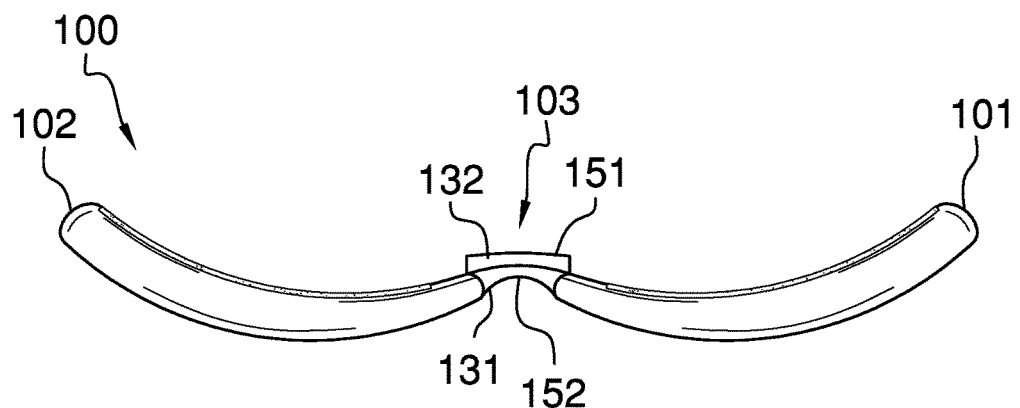
FIG. 2 is a top view of an embodiment of the disclosure.
Figure 3:
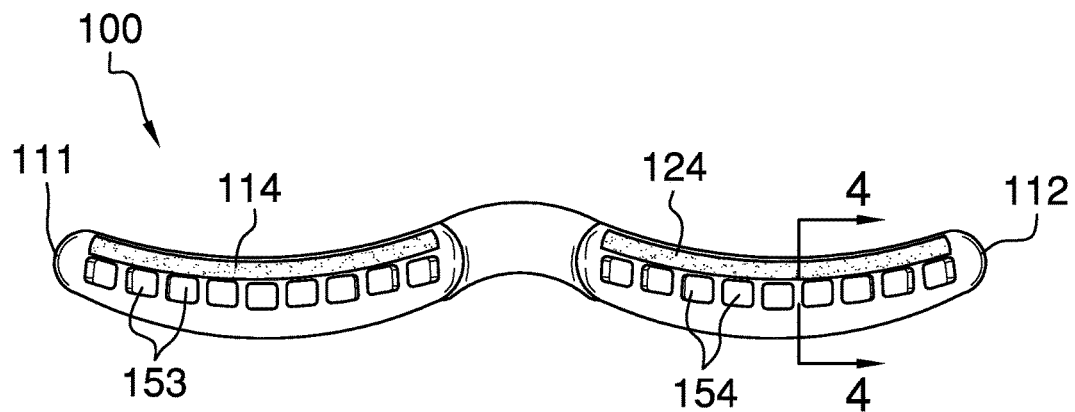
FIG. 3 is a back view of an embodiment of the disclosure.
Figure 4:
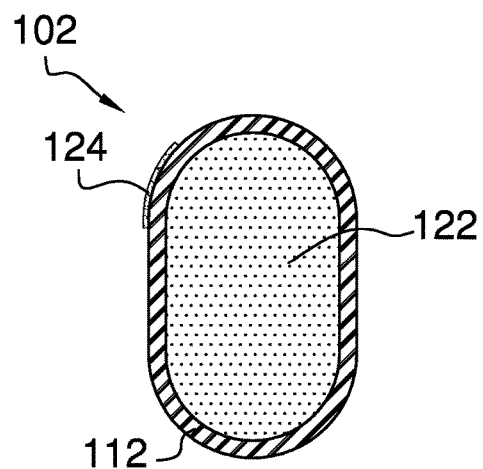
FIG. 4 is a cross-sectional view of an embodiment of the disclosure across 4-4 as shown in FIG. 3.
Figure 5:
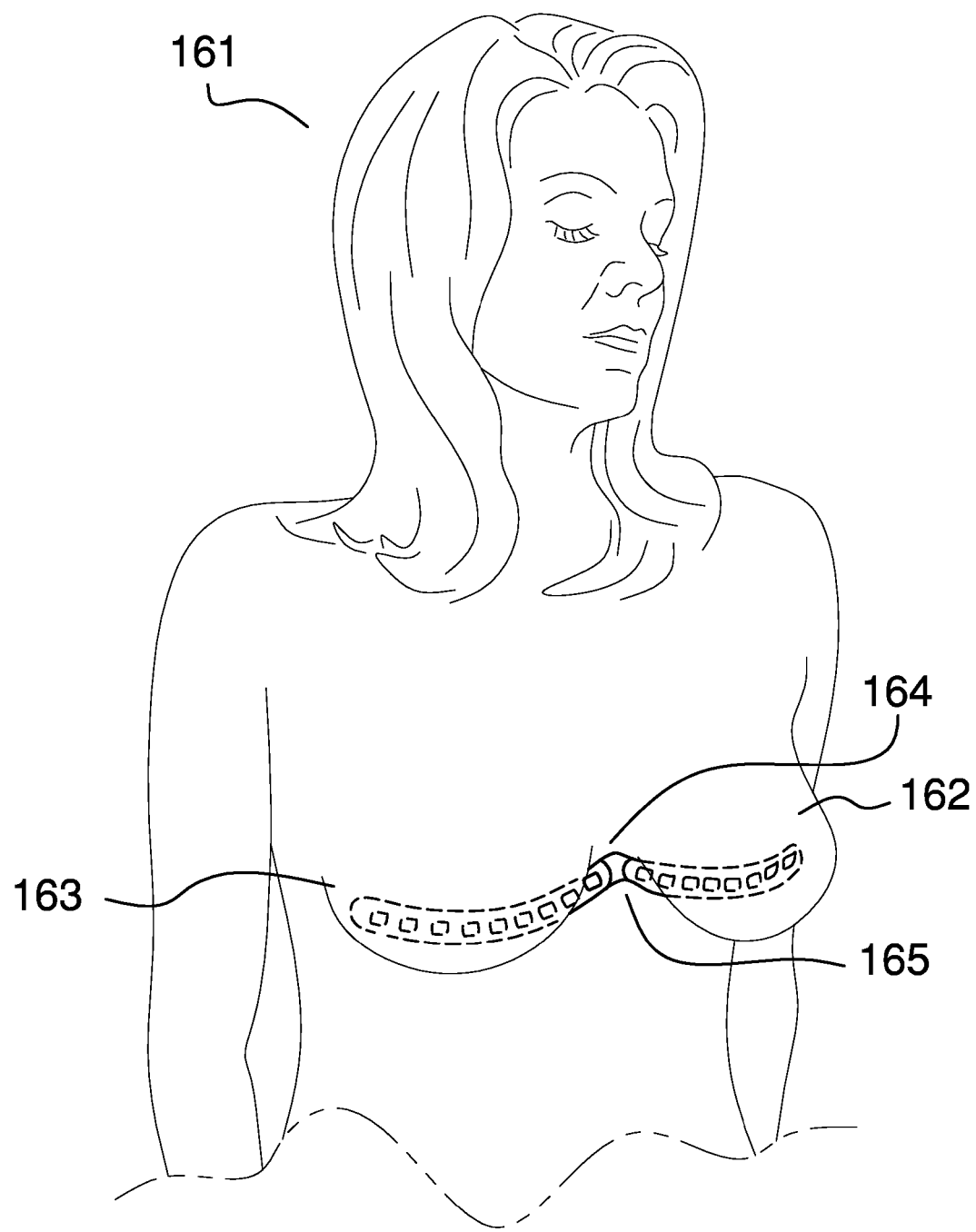
FIG. 5 is an in use view of an embodiment of the disclosure.

Detailed reference will now be made to one or more potential embodiments of the disclosure, which are illustrated in FIGS. 1 through 5.

The breast-lifting and cooling accessory 100 (hereinafter invention) is a therapeutic garment. The invention 100 is an item of underclothing. The invention 100 is configured for use with a woman 161. The woman 161 is further defined with a left breast 162, a right breast 163, an intermammary cleft 164, and a sternum 165. The invention 100 is a supporting garment that elevates the left breast 162 and the right breast 163 when a brassiere is not or is being worn. The invention 100 is a self-attaching garment. The invention 100 is a thermal structure that can further be used to cool the left breast 162 and the right breast 163 of the woman 161. The invention 100 comprises a left support 101, a right support 102, and a sternum 165 structure 103. The left support 101 and the right support 102 are joined at the sternum 165 structure 103.

The left support 101 is the structural member of the invention 100 that supports and cools the left breast 162 of the woman 161. The left support 101 is directly and removably attached to the left breast 162 of the woman 161. The left support 101 is further defined with a first end 141 and a second end 142. The left support 101 comprises a left shell 111, a left thermal gel 112, a left plurality of vents 113, and a left adhesive 114. The left shell 111 is further defined with a left cavity 153.

The left shell 111 is a hollow semi-rigid tubular structure. The semi-rigid structure of the left shell 111 is elastic in nature. The left shell 111 is a formed such that the left shell 111 forms a teardrop curve. The teardrop curve is described in greater detail elsewhere in this disclosure. The parameters of the teardrop curve selected for the left shell 111 are selected such that the curvature of the left shell 111 conforms to the natural curvature of the left breast 162 of the woman 161.

The left shell 111 is placed over the anterior portion of the left breast 162 such that the left shell 111 mildly compresses the left breast 162. The compression of the left breast 162 redistributes the mass of the left breast 162 such that a greater proportion of the mass is supported by the body of the woman 161. Alternatively, the left shell 111 is placed underneath the left breast 162 such that the left shell 111 forms a load path from the left breast 162 of the woman 161 to the sternum 165 of the woman 161 that supports the left breast 162.

The left cavity 153 refers to the hollow interior of the left shell 111. The left cavity 153 contains the left thermal gel 112. The left thermal gel 112 is a heat exchange medium that can be chilled before use of the invention 100. The cooled left thermal gel 112 acts as a thermal mass within the left cavity 153 of the left shell 111 that cools the left breast 162 of the woman 161. In the first potential embodiment of the disclosure, the left thermal gel 112 is a gel selected from the group consisting of 2-hydroxyethyl cellulose (CAS 9004-62-0) or silica gel (CAS 7631-86-9). The left thermal gel 112 can be prepared for use by placing the invention 100 in a refrigerated environment. It is preferred that the refrigerated environment be at or below a temperature of +5 F (−15 C). The left cavity 153 of the left shell 111 contains the left thermal gel 112.

The left plurality of vents 113 is a plurality of apertures that are formed in the surface of the left shell 111 that is placed against the left breast 162 of the woman 161. The purpose of the left plurality of vents 113 is to improve the efficiency of the heat exchange between the left breast 162 and the left thermal gel 112.

The left adhesive 114 is a commercially available removable adhesive that is applied to the exterior surface of the left shell 111. The left adhesive 114 secures the left shell 111 to the left breast 162 of the woman 161.

The right support 102 is the structural member of the invention 100 that supports and cools the right breast 163 of the woman 161. The right support 102 is directly and removably attached to the right breast 163 of the woman 161. The right support 102 is further defined with a third end 143 and a fourth end 144. The right support 102 comprises a right shell 121, a right thermal gel 122, a right plurality of vents 123, and a right adhesive 124. The right shell 121 is further defined with a right cavity 154.

The right shell 121 is a hollow semi-rigid tubular structure. The semi-rigid structure of the right shell 121 is elastic in nature. The right shell 121 is a formed such that the right shell 121 forms a teardrop curve. The teardrop curve is described in greater detail elsewhere in this disclosure. The parameters of the teardrop curve selected for the right shell 121 are selected such that the curvature of the right shell 121 conforms to the natural curvature of the right breast 163 of the woman 161.

The right shell 121 is placed over the anterior portion of the right breast 163 such that the right shell 121 mildly compresses the right breast 163. The compression of the right breast 163 redistributes the mass of the right breast 163 such that a greater proportion of the mass is supported by the body of the woman 161. Alternatively, the right shell 121 is placed underneath the right breast 163 such that the right shell 121 forms a load path from the right breast 163 of the woman 161 to the sternum 165 of the woman 161 that supports the right breast 163.

The right cavity 154 refers to the hollow interior of the right shell 121. The right cavity 154 contains the right thermal gel 122. The right thermal gel 122 is a heat exchange medium that is chilled before use of the invention 100. The cooled right thermal gel 122 acts as a thermal mass within the right cavity 154 of the right shell 121 that cools the right breast 163 of the woman 161. In the first potential embodiment of the disclosure, the right thermal gel 122 is a gel selected from the group consisting of 2-hydroxyethyl cellulose (CAS 9004-62-0) or silica gel (CAS 7631-86-9). The right thermal gel 122 can be prepared for use by placing the invention 100 in a refrigerated environment. It is preferred that the refrigerated environment be at or below a temperature of +5 F (−15 C). The right cavity 154 of the right shell 121 contains the right thermal gel 122.

The right plurality of vents 123 is a plurality of apertures that are formed in the surface of the right shell 121 that is placed against the right breast 163 of the woman 161. The purpose of the right plurality of vents 123 is to improve the efficiency of the heat exchange between the right breast 163 and the right thermal gel 122.

The right adhesive 124 is a commercially available removable adhesive that is applied to the exterior surface of the right shell 121. The right adhesive 124 secures the right shell 121 to the right breast 163 of the woman 161.

The sternum 165 structure 103 is the structural member of the invention 100 that: 1) attaches the left support 101 to the right support 102 to form an integrated unit; and, 2) anchors the invention 100 to the sternum 165 of the woman 161. The sternum 165 structure 103 is further defined with a fifth end 145, a sixth end 146, a proximal surface 151, and a distal surface 152. The sternum 165 structure 103 comprises a sternum 165 plate 131 and a sternum 165 adhesive 132. The proximal surface 151 is the surface of the sternum 165 plate 131 that is placed against the sternum 165 of the woman 161. The distal surface 152 is the surface of the sternum 165 plate 131 that is distal from the proximal surface 151.

The sternum 165 plate 131 is the structure of the invention 100 that attaches the left support 101 to the right support 102. The sternum 165 plate 131 forms the final link of the load path that: 1) distributes a portion of the load of the left breast 162 to the sternum 165; and, 2) distributes a portion of the load of the right breast 163 to the sternum 165. The sternum 165 plate 131 is a curved structure wherein the curves of the sternum 165 plate 131: 1) match the curvature of the sternum 165 of the woman 161; and, 2) performs a decorative function that allows the visible portions of the invention 100 to present the appearance of a single curved surface.

The sternum 165 adhesive 132 is a commercially available removable adhesive that is applied to the proximal surface 151 of the sternum 165 plate 131. The sternum 165 adhesive 132 removable attaches the proximal surface 151 of the sternum 165 plate 131 to the sternum 165 of the woman 161.

The first end 141 is the free end of the left shell 111. The second end 142 is the end of the left shell 111 that attaches to the fifth end 145 of the sternum 165 plate 131. The third end 143 is the end of the right shell 121 that attaches to the sixth end 146 of the sternum 165 plate 131. The fourth end 144 is the free end of the right shell 121.

The following definitions and directional references were used in this disclosure:

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Anchor: As used in this disclosure, anchor means to hold an object firmly or securely.

Anchor Point: As used in this disclosure, an anchor point is a location to which a first object can be securely attached to a second object.

Anterior: As used in this disclosure, anterior is a term that is used to refer to the front side or direction of an object. When comparing two objects, the anterior object is the object that is closer to front of the object.

Decorative: As used in this disclosure, the term decorative is used to describe a design decision or feature that is made for aesthetic purposes and is not anticipated to materially affect the novelty of the innovation described in this disclosure.

Inferior: As used in this disclosure, the term inferior refers to a directional reference that is parallel to and in the same direction as the force of gravity.

Load Path: As used in this disclosure, a load path refers to a chain of one or more structures that transfers a load generated by a raised structure or object to a foundation, supporting surface, or the earth.

Posterior: As used in this disclosure, posterior is a term that is used to refer to the side of an object that is distal or in the opposite direction of the anterior side. When comparing two items, the posterior item is the item that is distal from the front of the object.

Removable Adhesive: As used in this disclosure, a removable adhesive is a commercially available adhesive that is designed with a lower tack, or stickiness, such that a first object is attached to a second object with a removable adhesive the first object can be readily removed in a manner that ideally, though not necessarily practically, leaves behind no adhesive residue on the second object. A repositionable adhesive is a subset of removable adhesives that are intended to allow the first object to be reattached to a third object or the second object in the initial or a different position. Within this disclosure, a removable adhesive is assumed to include repositionable adhesives.

Semi-Rigid Structure: As used in this disclosure, a semi-rigid structure is a solid structure that is stiff but not wholly inflexible and that will deform under force before breaking. A semi-rigid structure may or may not behave in an elastic fashion in that a semi-rigid structure need not return to a relaxed shape.

Shell: As used in this disclosure, a shell is a structure that forms an outer covering intended to contain an object. Shells are often, but not necessarily, rigid or semi-rigid structures that are intended to protect the object contained within it.

Superior: As used in this disclosure, the term superior refers to a directional reference that is parallel to and in the opposite direction of the force of gravity.

Tack: As used in this disclosure, tack refers to a measure of the bonding strength of an adhesive. The greater the bonding strength the more tack the adhesive is said to have.

Teardrop Curve: As used in this disclosure, a teardrop curve refers to the curvature formed by a falling drop of water along a surface—such as a tear drop. The teardrop curve is well described by the equation: $y^2=x^m*(1-x)$ ($0<x<1$); or the equivalent parametric equations: $x=\cos(t)$ and $y=\sin(t)*\sin^{m-1}(0.5*t)$. Within this mathematical description, the x axis bifurcates the teardrop along the length of the tear drop. Values of m can vary, but a value between greater than 2 and less than 8 are suitable for most purposes.

Therapeutic: As used in this disclosure, therapeutic is an adjective that refers to a medical, ameliorative, or hygienic substance, process, or procedure.

Underclothing: As used in this disclosure, underclothing refers to garments that are intended to be worn next to the skin. Underclothing is often worn in conjunction with an outer layer of clothing.

The directional references used in this disclosure correspond to the directional references from the perspective of a person when the invention 100 is worn normally. As such, left refers to the direction towards the left side of the person and right refers to the direction towards the right side of the person. Superior refers to the direction towards the head of the wearer and inferior refers to the direction towards the feet of the wearer. Anterior refers to front side of the person and posterior refers to the back side of the person.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A therapeutic garment comprising:
wherein the therapeutic garment comprises a left support, a right support, and a sternum structure;
wherein the sternum structure attaches the left support to the right support to form an integrated unit;
wherein the therapeutic garment is configured for use with a woman;
wherein the woman is further defined with a left breast, a right breast, an intermammary cleft, and a sternum;
wherein the therapeutic garment is a supporting garment that supports the left breast;
wherein the therapeutic garment is a supporting garment that supports the right breast;
wherein the therapeutic garment is a self-attaching garment;
wherein the therapeutic garment cools the left breast;
wherein the therapeutic garment cools the right breast;
wherein the left support supports and cools the left breast;
wherein the left support is directly and removably attached to the left breast;
wherein the right support supports and cools the right breast;
wherein the right support is directly and removably attached to the right breast;
wherein the left support is further defined with a first end and a second end;
wherein the right support is further defined with a third end and a fourth end;
wherein the sternum structure anchors the therapeutic garment to the sternum;
wherein a sternum plate forms a final link of a load path that distributes a portion of the load of the left breast to the sternum;

wherein the sternum plate forms the final link of the load path that distributes a portion of the load of the right breast to the sternum;
wherein the sternum structure is further defined with a fifth end, a sixth end, a proximal surface, and a distal surface;
wherein the left support comprises a left shell, a left thermal gel, a left plurality of vents, and a left adhesive;
wherein the left plurality of vents and the left adhesive are formed in the left shell;
wherein the left thermal gel is contained within the left shell;
wherein the left shell is further defined with a left cavity.

2. The therapeutic garment according to claim 1
wherein the left shell is a semi-rigid tubular structure;
wherein the semi-rigid tubular structure of the left shell is elastic in nature;
wherein the left shell is a hollow structure;
wherein the left cavity refers to a hollow interior of the left shell.

3. The therapeutic garment according to claim 2 wherein the left shell is a formed such that the left shell forms a teardrop curve;
wherein a parameters of the teardrop curve selected for the left shell are selected such that a curvature of the left shell conforms to the curvature of the left breast.

4. The therapeutic garment according to claim 3
wherein the left cavity contains the left thermal gel;
wherein the left thermal gel is a heat exchange medium;
wherein the left thermal gel is capable of being chilled before use of the therapeutic garment;
wherein when chilled, the cooled left thermal gel acts as a thermal mass within the left cavity of the left shell that cools the left breast;
wherein the left cavity of the left shell contains the left thermal gel.

5. The therapeutic garment according to claim 4
wherein each of the left plurality of vents is an aperture that is formed in a surface of the left shell that is placed against the left breast;
wherein the left adhesive is a removable adhesive;
wherein the left adhesive is applied to an exterior surface of the left shell;
wherein the left adhesive secures the left shell to the left breast.

6. The therapeutic garment according to claim 5
wherein the right support comprises a right shell, a right thermal gel, a right plurality of vents, and a right adhesive;
wherein the right plurality of vents and the right adhesive are formed in the right shell;
wherein the right thermal gel is contained within the right shell;
wherein the right shell is further defined with a right cavity.

7. The therapeutic garment according to claim 6
wherein the right shell is a semi-rigid tubular structure;
wherein the semi-rigid structure of the right shell is elastic in nature;
wherein the right shell is a hollow structure;
wherein the right cavity refers to a hollow interior of the right shell.

8. The therapeutic garment according to claim 7,
wherein the right shell is formed such that the right shell forms a teardrop curve;
wherein a parameters of the teardrop curve selected for the right shell are selected such that a curvature of the right shell conforms to a curvature of the right breast.

9. The therapeutic garment according to claim 8
wherein the right cavity contains the right thermal gel;
wherein the right thermal gel is a heat exchange medium;
wherein the right thermal gel is chilled before use of the therapeutic garment;
wherein the chilled right thermal gel acts as a thermal mass within the right cavity of the right shell that cools the right breast;
wherein the right cavity of the right shell contains the right thermal gel.

10. The therapeutic garment according to claim 9
wherein each of the right plurality of vents is an aperture that is formed in a surface of the right shell that is placed against the right breast;
wherein the right adhesive is a removable adhesive;
wherein the right adhesive is applied to an exterior surface of the right shell;
wherein the right adhesive secures the right shell to the right breast.

11. The therapeutic garment according to claim 10
wherein the sternum structure comprises a sternum plate and a sternum adhesive;
wherein the sternum adhesive attaches the sternum plate to the sternum.

12. The therapeutic garment according to claim 11
wherein the sternum plate is a curved structure;
wherein the curvature of the sternum plate matches a curvature of the sternum;
wherein the sternum adhesive is a removable adhesive that is applied to a proximal surface of the sternum plate;
wherein the sternum adhesive removable attaches the proximal surface of the sternum plate to the sternum.

13. The therapeutic garment according to claim 12
wherein the left shell is placed over an anterior portion of the left breast;
wherein the right shell is placed over an anterior portion of the right breast.

14. The therapeutic garment according to claim 13
wherein the left thermal gel comprises 2-hydroxyethyl cellulose;
wherein the right thermal gel comprises 2-hydroxyethyl cellulose.

15. The therapeutic garment according to claim 13
wherein the left thermal gel comprises silica gel;
wherein the right thermal gel comprises silica gel.

16. The therapeutic garment according to claim 12
wherein the left shell is placed underneath the left breast such that the left shell forms a load path from the left breast to the sternum that supports the left breast;
wherein the right shell is placed underneath the right breast such that the right shell forms a load path from the right breast to the sternum that supports the right breast.

17. The therapeutic garment according to claim 16
wherein the left thermal gel comprises 2-hydroxyethyl cellulose;
wherein the right thermal gel comprises 2-hydroxyethyl cellulose.

18. The therapeutic garment according to claim 17
wherein the left thermal gel comprises silica gel;
wherein the right thermal gel comprises silica gel.

* * * * *